(12) United States Patent
zur Megede et al.

(10) Patent No.: US 10,809,250 B2
(45) Date of Patent: Oct. 20, 2020

(54) DIGITAL IMMUNOASSAY

(71) Applicant: Bio-Rad Laboratories, Inc., Hercules, CA (US)

(72) Inventors: Jan zur Megede, Hercules, CA (US); George Karlin-Neumann, Hercules, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 164 days.

(21) Appl. No.: 15/752,108

(22) PCT Filed: Aug. 18, 2016

(86) PCT No.: PCT/US2016/047574
§ 371 (c)(1),
(2) Date: Feb. 12, 2018

(87) PCT Pub. No.: WO2017/034925
PCT Pub. Date: Mar. 2, 2017

(65) Prior Publication Data
US 2018/0238865 A1    Aug. 23, 2018

Related U.S. Application Data

(60) Provisional application No. 62/209,731, filed on Aug. 25, 2015.

(51) Int. Cl.
*G01N 33/542* (2006.01)
*G01N 33/58* (2006.01)

(52) U.S. Cl.
CPC ......... *G01N 33/542* (2013.01); *G01N 33/581* (2013.01); *G01N 33/582* (2013.01); *G01N 2333/57* (2013.01); *G01N 2333/575* (2013.01)

(58) Field of Classification Search
None
See application file for complete search history.

(56) References Cited

U.S. PATENT DOCUMENTS

| 5,434,088 A | 7/1995 | Ikeda et al. |
| 5,981,180 A | 11/1999 | Chandler et al. |

(Continued)

FOREIGN PATENT DOCUMENTS

| WO | 2012135259 A1 | 10/2012 |
| WO | 2012135327 A1 | 10/2012 |

(Continued)

OTHER PUBLICATIONS

Abe, R., et al., ""Quenchbodies": Quench-Based Antibody Probes That Show Antigen-Dependent Fluorescence," Journal of the American Chemical Society, Oct. 6, 2011, vol. 133, pp. 17386-17394.
Jeong, H., et al., "Strategy for Making a Superior Quenchbody to Proteins: Effect of the Fluorophore Position" Sensors, 2014, vol. 14. pp. 13285-13297.

(Continued)

*Primary Examiner* — Changhwa J Cheu
(74) *Attorney, Agent, or Firm* — Kilpatrick Townsend and Stockton LLP

(57) ABSTRACT

Methods of detecting an analyte in a sample are provided. In one embodiment, the method comprises forming a partition comprising the sample, a binding agent capable of emitting a signal when bound to the analyte, and a marker capable of identifying the partition; allowing the binding agent to bind to the analyte, if present; and detecting the presence of the analyte in the sample by detecting the signal emitted from the binding agent in the partition.

19 Claims, 6 Drawing Sheets

(56) References Cited

U.S. PATENT DOCUMENTS

| | | |
|---|---|---|
| 2008/0199972 A1 | 8/2008 | Sellrie |
| 2012/0122714 A1 | 5/2012 | Samuels et al. |
| 2012/0132288 A1 | 5/2012 | Weitz et al. |
| 2012/0194805 A1* | 8/2012 | Ness ............ G01N 21/05 356/213 |
| 2012/0264646 A1 | 10/2012 | Link et al. |
| 2012/0270338 A1 | 10/2012 | Ueda et al. |
| 2014/0228239 A1* | 8/2014 | McCoy ............ C12Q 1/00 506/9 |
| 2014/0329228 A1* | 11/2014 | Ueda ............ G01N 33/582 435/5 |
| 2015/0024945 A1 | 1/2015 | Healy |

FOREIGN PATENT DOCUMENTS

| | | |
|---|---|---|
| WO | 2012/167142 A2 | 12/2012 |
| WO | 2014117088 A1 | 7/2014 |
| WO | 2014/182835 A1 | 11/2014 |

OTHER PUBLICATIONS

International Search Report dated Oct. 27, 2016, for corresponding international patent application number: PCT/US2016/047574, filed on Aug. 18, 2016, 13 pp.

European Patent App. No. 16839851.9, Extended European Search Report dated Apr. 15, 2019.

Elizabeth M. Miller, et al., "A Digital Microfluidic Approach to Heterogeneous Immunoassays," Analytical and Bioanalytical Chemistry, vol. 399, No. 1, Nov. 2010, pp. 337-345.

Patrick A. Sandoz, et al., "Digital Readout Platform for Water-In-Oil Droplet Immunoassays Running on a Cell-Phone for Point of Care Viral Load Sensing," Miniaturized Sensing for Chemistry and Life Sciences, Nov. 2012, pp. 338-340.

Jung-Uk Shim, et al., "Ultrarapid Generation of Femtoliter Microfluidic Droplets for Single-Molecule-Counting Immunoassays," ACS NANO, vol. 7, No. 7, Jul. 2013, pp. 5955-5964.

Ramakrishna S. Sista, et al., "Heterogeneous Immunoassays Using Magnetic Beads on a Digital Microfluidic Platform," Lab on a Chip, vol. 8, No. 12, Jan. 2008, pp. 2188-2196.

* cited by examiner

DIGITAL IMMUNOASSAY

CROSS-REFERENCE TO RELATED APPLICATIONS

This application is a U.S. National Phase application under 35 U.S.C. § 371 of International Application No. PCT/US2016/047574, filed Aug. 18, 2016, which claims benefit of priority of U.S. Provisional Application No. 62/209,731, filed Aug. 25, 2015, the disclosure of which are herein incorporated by reference in their entirety.

BACKGROUND

The quantification of antigens in a sample can provide useful information for a number of clinical applications. One method for detecting and quantifying antigens is by enzyme-linked immunosorbent assay (ELISA). During an ELISA, a sample containing an analyte is subjected to a biochemical process taking place on an insoluble carrier surface such as a microwell in a microtiter plate. Depending on the particular test being conducted, a predetermined capture antibody or bio-molecule (e.g., antigen) may be immobilized on the surface of each microwell, and controlled amounts of various fluids (e.g. blocking solution, washing solution, test sample, detection antibody, primary and secondary antibodies, and substrate) may be added to the microwell according to a predetermined protocol that includes separate incubation and wash steps. The result of the biochemical process may be viewed using an optical detector measuring absorbance, fluorescence, and/or luminescence, or other properties, to provide a qualitative and/or quantitative test result.

Although ELISAs provide useful information, the technique is time consuming due to the long incubation times during each assay step. Also, the limits of detection and precision of quantification that can be achieved with this assay format are not sufficient for many applications. Another disadvantage is that ELISAs are difficult to scale to high-level multiplexing due to antibody cross-reactivity and non-specific adsorption occurring when assays are multiplexed in the same microwell.

SUMMARY

Disclosed herein are methods of detecting an analyte in a sample. In some embodiments, the method comprises forming a partition comprising the sample, a binding agent capable of emitting a signal when bound to the analyte, and a marker capable of identifying the partition; allowing the binding agent to bind to the analyte, if present; and detecting the presence of the analyte in the sample by detecting the signal emitted from the binding agent in the partition. In some embodiments, the method further includes identifying the partition by detecting the marker. In an embodiment, the binding agent is a quenchbody. In some embodiments, the partition further comprises a substrate and the binding agent is an antibody labeled with an enzyme capable of converting the substrate into a molecule that produces a signal when the antibody binds to the analyte. In some embodiments, the enzyme is capable of converting the substrate into an intermediate that is further converted into the molecule that produces the signal.

In some embodiments, the method comprises forming a partition comprising the sample, a binding agent capable of quenching a signal when bound to the analyte, and a marker capable of identifying the partition; allowing the binding agent to bind to the analyte, if present; and detecting the presence of the analyte in the sample by detecting the quenching of the fluorescent signal from the binding agent in the partition. In some embodiments, the method further includes identifying the partition by detecting the marker. In an embodiment, the binding agent is an analyte-specific antibody pair comprising a first antibody having a fluorescent label and a second antibody having a quencher, wherein a fluorescent signal from the first antibody is quenched by the second antibody when the analyte-specific antibody pair is bound to the analyte.

In certain embodiments, the forming a partition step comprises injecting the sample, binding agent and marker into the partition in any order or simultaneously. In some embodiments, the forming a partition step comprises forming a sample partition and injecting the binding agent and the marker into the sample partition. In some embodiments, the forming a partition step comprises forming a binding agent partition and injecting the sample and the marker into the binding agent partition. In some embodiments, the forming a partition step comprises forming a marker partition and injecting the sample and the binding agent into the marker partition.

In some embodiments, the method comprises forming a partition comprising the sample and a quenchbody capable of emitting a fluorescent signal when bound to the analyte; allowing the quenchbody to bind to the analyte, if present; and detecting the presence of the analyte in the sample by detecting the fluorescent signal emitted from the quenchbody in the partition. In certain embodiments, the forming a partition step comprises injecting the sample and the quenchbody into the partition in any order or concurrently. In some embodiments, the forming a partition step comprises forming a sample partition followed by injecting the quenchbody into the sample partition. In some embodiments, the forming a partition step comprises forming a quenchbody partition followed by injecting the sample into the quenchbody partition. In some embodiments, the method further comprises injecting the partition with a marker capable of identifying the partition; and responsive to detecting the marker, identifying the partition. In some embodiments, injecting the partition with a marker is concurrent with injecting the partition with the sample and the quenchbody. In some embodiments, injecting the partition with a marker is subsequent to injecting the partition with the sample and the quenchbody. In some embodiments, injecting the partition with a marker is prior to injecting the partition with the sample and the quenchbody In some embodiments, the marker is a fluorophore. In some embodiments, the partition is a droplet surrounded by a carrier fluid (e.g., oil).

In certain embodiments, the analyte is selected from the group consisting of proteins, peptides, hormones, antibodies and antibody fragments. In some embodiments, the sample is selected from the group consisting of a protein solution, a peptide solution, cell extract, whole blood, plasma, serum, saliva, urine, milk, eggs and water.

DETAILED DESCRIPTION

Figure 1:
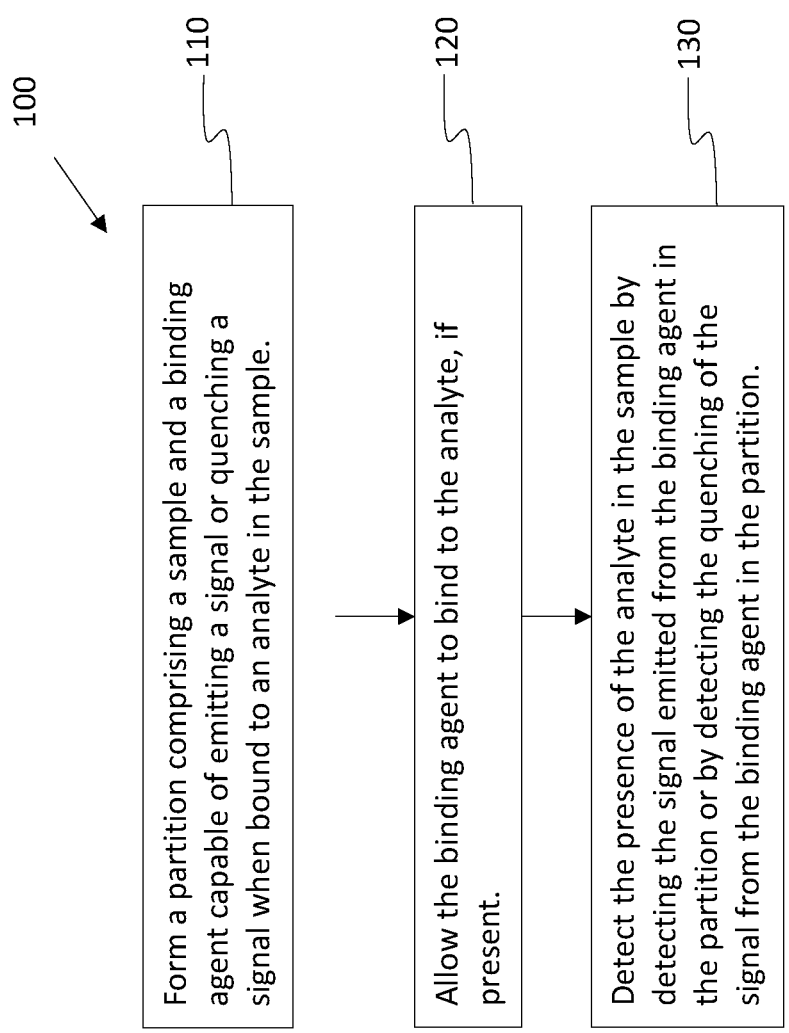
FIG. 1 is a flow chart showing a method of detecting an analyte in a sample according to an embodiment of the invention.

Provided herein are methods, compositions and kits for detecting one or more analytes (e.g., antigens) in a sample. Multiplex methods have been discovered that allow for simultaneous testing of multiple samples and/or analytes. As described herein, the methods are performed in partitions (for example, in droplets in an emulsion).

In some embodiments, the methods include forming partitions having a sample, a binding agent (e.g., a quenchbody, an antibody labeled with an enzyme, or an analyte-specific antibody pair) and a marker. After the binding agent is allowed to bind to the analyte, the partition is analyzed for the presence or absence of a signal, e.g., using digital analysis.

Also provided herein are libraries of partitions as well as systems for performing the methods and for analyzing results.

The methods described herein allow for improved sensitivity of detecting an analyte, precise quantification of the analyte, and lower limits of direct detection of analyte in a sample. The homogenous immunoassay methods described herein also use a liquid phase system requiring neither an immobilization step nor a washing step.

I. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "binding agent" refers to a molecule that specifically binds to an antigen. Exemplary binding agents include, but are not limited to, an antibody, an antibody fragment, a non-antibody protein scaffold, an antibody mimetic, an aptamer, an affimer, a quenchbody, an antibody labeled with an enzyme, or an analyte-specific antibody pair.

The term "antibody" refers to a polypeptide of the immunoglobulin family or a polypeptide comprising fragments of an immunoglobulin that is capable of noncovalently, reversibly, and in a specific manner binding to a corresponding antigen. The term includes, but is not limited to, polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompases conjugates, including but not limited to fusion proteins containing an immunoglobulin moiety (e.g., chimeric or bispecific antibodies or single chain Fv's (scFv's)), and fragments, such as Fab, F(ab')2, Fv, scFv, Fd, dAb and other compositions.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. The variable region contains the antigen-binding region of the antibody (or its functional equivalent) and is most critical in specificity and affinity of binding. See Paul, Fundamental Immunology (2003).

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., scFv) or those identified using phage display libraries (see, e.g., McCafferty et al. (1990) Nature 348:552-554). Methods for the preparation of antibodies are known in the art; see, e.g., Kohler & Milstein (1975) Nature 256:495-497; Kozbor et al. (1983) Immunology Today 4:72; Cole et al., Monoclonal Antibodies and Cancer Therapy, pp. 77-96. Alan R. Liss, Inc. 1985).

As used herein, the term "Fv" refers to a monovalent or bi-valent variable region fragment, and can encompass only the variable regions (e.g., $V_L$ and/or $V_H$), as well as longer fragments, e.g., an Fab, Fab' or F(ab')2, which also includes $C_L$ and/or $C_H1$. Unless otherwise specified, the term "Fc" refers to a heavy chain monomer or dimer comprising $C_H1$ and $C_H2$ regions.

The terms "antigen," "immunogen," "target," "analyte," and like terms are used herein to refer to a molecule, compound, or complex that is recognized by a binding agent, i.e., can be specifically bound by the binding agent. The term can refer to any molecule that can be specifically recognized by an binding agent, e.g., a protein, a polysaccharide, a toxin, a cell wall, a cell capsule, a viral capsule, a viral coat, a flagellum, a fimbria or pilus, a microorganism, a nucleic acid complexed to a protein or a polysaccharide, a lipid, a lipid complexed to a protein or a polysaccharide, a polynucleotide, a polypeptide, a carbohydrate, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

Antibodies bind to an "epitope" on an antigen. The epitope is the localized site on the antigen that is recognized and bound by the antibody. Protein epitopes can include a few amino acids or portions of a few amino acids, e.g., 5 or 6, or more, e.g., 20 or more amino acids, or portions of those amino acids. Epitopes can also include non-protein components, e.g., nucleic acid (e.g., RNA or DNA), carbohydrate, or lipid. Epitopes can also include combinations of these components. In some cases, the epitope is a three-dimensional moiety. Thus, for example, where the target is a protein target, the epitope can be comprised of consecutive amino acids, or amino acids from different parts of the protein that are brought into proximity by protein folding (e.g., a discontinuous epitope). The same is true for other types of target molecules, such as dsDNA and chromatin, that form three-dimensional structures.

The terms "specific for," "specifically binds," and like terms refer to a molecule (e.g., binding agent) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, a binding agent that specifically binds a particular target will typically bind the target with at least a 2-fold greater affinity than a non-target.

The term "binds" with respect to a target (e.g., antigen, analyte, epitope), typically indicates that an binding agent binds a majority of the antibody targets in a pure population, assuming an appropriate molar ratio of binding agent to target. For example, a binding agent that binds a given target typically binds to at least ⅔ of the targets in a solution (e.g., 75%, 80%, 85%, 90%, 91%, 92%, 93%, 94%, 95%, 96%, 97%, 98%, 99%, or 100%/). One of skill will recognize that some variability will arise depending on the method and/or threshold of determining binding.

The terms "label" and "detectable label" interchangeably refer to a composition detectable by spectroscopic, photochemical, biochemical, immunochemical, chemical, or other physical means. For example, useful labels include fluorescent dyes (fluorophores), fluorescent quenchers, luminescent agents, electron-dense reagents, enzymes (e.g., as commonly used in an ELISA), biotin, digoxigenin, $^{32}P$ and other isotopes, haptens, proteins, nucleic acids, or other substances which may be made detectable, e.g., by incorporating a label into an oligonucleotide, peptide, or antibody specifically reactive with a target molecule. The term includes combinations of single labeling agents, e.g., a combination of fluorophores that provides a unique detectable signature, e.g., at a particular wavelength or combination of wavelengths.

A molecule that is "linked" to a label (e.g., as for a labeled antibody as described herein) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "partitioning" or "partitioned" refers to separating an aqueous solution having one or more of a sample, reactant and marker (or identifier) into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used in this specification and the appended claims, the singular forms "a", "an", and "the" include plural referents unless the content clearly dictates otherwise. Thus, for example, reference to a system comprising "a binding agent" includes a system comprising one or more binding agent. Likewise, reference to "a substance" includes one or more substances.

II. Methods

Referring to FIG. 1, a method 100 of detecting an analyte in a sample will now be described. The steps may be performed in any suitable order, in any suitable combination, and may be combined with or modified by any other suitable aspects of the disclosure provided herein.

A. Partition Formation

In exemplary step 110, a partition is formed. In some embodiments, the partition includes a sample having an analyte, and a binding agent capable of emitting or quenching a signal when bound to the analyte. In some embodiments, the partition further includes a marker capable of identifying the partition.

The partition can include any of a number of types of partitions, including solid partitions (e.g., wells or tubes) and fluid partitions (e.g., aqueous phase or droplet within an oil phase). In some embodiments, the partitions are droplets. In some embodiments, the partitions are microchannels. Methods and compositions for partitioning a sample are described, for example, in published patent applications WO 2012/135259, WO 2014/117088, WO 2010/036352, and US 2010/0173394, the entire content of each of which is incorporated by reference herein.

In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated coalesce with other droplets.

In an embodiment, the droplet is formed by flowing an oil phase through an aqueous phase. The oil for the oil phase may be synthetic or naturally occurring. In some embodiments, the oil comprises carbon and/or silicon. In some embodiments, the oil comprises hydrogen and/or fluorine. Exemplary oils include, but are not limited to, silicone oil, mineral oil, fluorocarbon oil, vegetable oil, or a combination thereof.

The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the droplet is formed by flowing an oil phase through an aqueous phase having a sample and/or one or more components (e.g., reagents) that are used to detect an analyte in the sample. In some embodiments, the one or more components used to detect an analyte in the aqueous droplet are soluble and/or miscible in water including, but not limited to, one or more salts, buffering agents, reagents (e.g., binding agents and/or markers), surfactants, and/or whatever additional components may be necessary for a desired reaction(s) that may be intended to occur within a formed droplet. All such additional components may be selected to be compatible with the desired reaction or intended assay.

Figure 2:
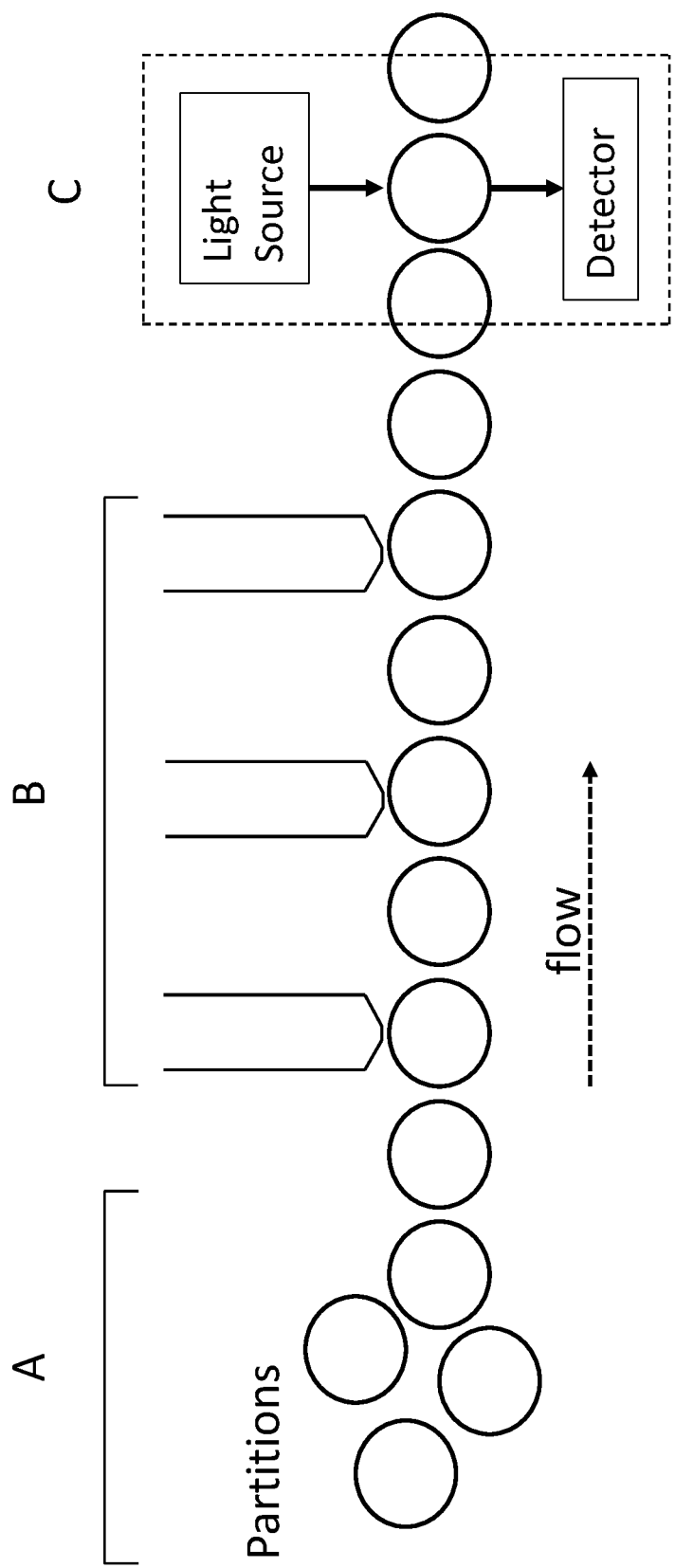
FIG. 2 is a schematic view of a microfluidic device that may be used in methods according to embodiments of the invention. Reservoir A contains partitions with aqueous phase assay components (e.g., a sample, a binding agent capable of emitting a signal when bound to an analyte and/or a marker capable of identifying the partition). Injection point B is where at least one of another assay component is injected into each of the partitions. The partitions flow downstream to Point C where the partition is exposed to a light source and if an analyte of interest is present in a partition, a detector detects an optical signal emitted from the partition.

Referring to FIG. 2, a partition (e.g., droplet) having a sample and/or one or more assay components may be provided in reservoir A. In some embodiments in which the droplet is provided with a buffering agent, at least one of a sample having an analyte, a binding agent and/or a marker are injected into the partition at injection point B. The sample, binding agent and marker may be injected into the partition in any order or simultaneously. In some embodiments, a sample is injected into the partition followed by a binding agent and then a marker. In certain embodiments, a binding agent is injected into the partition followed by a sample and then a marker. In some embodiments, a marker is injected into the partition followed by a sample and then a binding agent.

In some embodiments in which a partition in reservoir A is formed from an aqueous phase having a sample, a binding agent and a marker are injected into the partition at injection point B in any order or simultaneously. In certain embodiments in which a partition in reservoir A is formed from an aqueous phase having a marker, a sample and a binding agent are injected into the partition at injection point B in any order or simultaneously. In some embodiments in which a partition is formed from an aqueous phase having a binding agent, a sample and a marker are injected into the partition at injection point B in any order or simultaneously.

Methods of injecting fluids into partitions are described in, for example, WO 2012/135259 and US 2012/0132288, each of which is incorporated by reference in its entirety.

In some embodiments, the sample and/or binding agent is diluted prior to partition formation. Dilution or other ways of varying concentration of one or more components of the reaction mixture is one way to improve estimates of the analyte concentration. Dilution can be achieved by physically diluting the sample to different extents, or by virtual dilution by changing the volume assayed in each partition. In some embodiments, partitions of two or more partition sizes are generated. For example, a device that partitions the sample into two or more partition sizes, such as a droplet generator that produces at least two different sizes of monodisperse droplets, an emulsion that generates polydisperse droplets, or a plate with at least two volumes for partitioning the sample, can be used. In certain embodiments, the sample is diluted after injection into the droplet by, for example, droplet inflation as described in WO 2014/117088, the contents of which are incorporated herein by reference.

Dilution reduces background, but can affect dynamic range unless the number of partitions is increased as well. One solution is to increase the number of partitions, but other solutions may help as well. Use of different concentrations either globally (i.e., all components are diluted) or by diluting a subset of the reaction components is contemplated. In some embodiments, comparing a partition with sample to a no sample control partition is used to determine the background vs. signal. In other embodiments, the concentrations of the other components are changed. In some cases, the binding characteristics of each binding agent will be different. In some embodiments, running the same sample at different concentrations of sample, or different concentrations of one or more binding agent, generates different effects for specific vs. non-specific binding. In some embodiments, increasing (for example doubling) the binding agent concentration has a very specific effect on the random distribution causing that number to nearly double (with the precise increase predictable by poisson statistics for a given number of partitions), but has a limited effect on the specific binding as long as the binding agent concentration is saturating for that target. Likewise, in some embodiments, decreasing binding agent concentration has one effect on the non-specific binding and a different effect of the specific binding of the binding agent.

In some embodiments, at least 500 partitions (e.g., droplets), at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions are formed.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Sample

The methods described herein can be used to detect one or more analytes in any type of sample. In some embodiments, the sample is a biological sample. Biological samples can be obtained from any biological organism, e.g., an animal, plant, fungus, bacterial, or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, transformed cells, stem cells, stool, or urine.

In some embodiments, the one or more analytes to be detected are peptides, proteins (e.g., antibodies, enzymes, growth regulators, clotting factors, or phosphoproteins), immunogens, polysaccharides, toxins, cell walls, cell capsules, viral capsules, viral coats, flagellae, fimbriae or pili, microorganisms, nucleic acids complexed to protein or polysaccharide, or lipids complexed to protein or polysaccharide.

In some embodiments, two, three, four, five, or more different analytes are to be detected. In some embodiments, wherein two or more different analytes are to be detected, the two or more different analytes are the same type of analytes (e.g., two or more proteins present in a complex). In some embodiments, wherein two or more different analytes are to be detected, the two or more different analytes are different types of analytes.

In some embodiments, the sample can be prepared to improve the efficient detection of the analyte (s). For example, in some embodiments the sample can be fragmented, fractionated, homogenized, or sonicated. In some embodiments, an analyte of interest, or a sub-fraction comprising the analyte of interest, can be extracted or isolated from a sample (e.g., a biological sample). In some embodiments, the sample is enriched for the presence of the one or more analytes. In some embodiments, the analyte is enriched in the sample by an affinity method, e.g., immunoaffinity enrichment. In some embodiments, the analyte is enriched in the sample using size selection (e.g., removing very small fragments or molecules or very long fragments or molecules).

Binding Agent

A binding agent suitable for use according to the methods described herein is any molecule that specifically binds to an analyte (i.e., antigen) of interest.

In some embodiments, the binding agent as described herein is linked to a detectable label. The label can be linked directly to the binding agent (e.g., by a covalent bond) or the attachment can be indirect (e.g., using a chelator or linker molecule). The terms "label" and "detectable label" are used synonymously herein.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FAM, FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), pyrene butyrate, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. Intercalating dyes include, but are not limited to, SYBR Green and Pico Green (from Molecular Probes, Inc., Eugene. Oreg.), ethidium bromide, propidium iodide, chromomycin, acridine orange, Hoechst 33258, TOTO-I, YOYO-1, and DAPI (4′,6-diamidino-2-phenylindole hydrochloride).

In some embodiments, a fluorescent agent is a polymer dot or a quantum dot. The particular quantum dot (QD) employed is not critical to the present invention. Quantum dots are known in the art and are described, for example, by Han et al., "Quantum-dot-tagged Microbeads for Multiplexed Optical Coding of Biomolecules". Nat Biotechnol (July 2001) vol. 19, pp. 631-635. One of skill in the art will appreciate the various quantum dots that may serve as fluorescent labels and that can be employed in embodiments of the invention and which are available from various commercial vendors. Exemplary quantum dots (QDs) include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS Lumidots™ and CdSe/ZnS NanoDots™, 480-640 nm emission spectra, Sigma-Aldrich®); and cadmium-free quantum dots (e.g., CFQD™, 400-650 nm emission spectra, Sigma-Aldrich®).

In an embodiment, the label is a fluorophore and the fluorophore is present in a sufficient amount such that the fluorophore is detectable. In an embodiment, at least 1 fluorophore to 100 fluorophores, 100 fluorophores to 1000 fluorophores, 1000 fluorophores to 10000 fluorophores, 10000 fluorophores to 100000 fluorophores, 100000 fluorophores to 1 million fluorophores, 1 million fluorophores to 10 million fluorophores or at least 10 million fluorophores to 100 million fluorophores are present per partition having a 1 nanoliter volume. In embodiments having a partition volume less than 1 nanoliter, less fluorophores are present per partition (e.g., 1 to 100 fluorophores per 50 femtoliter partition volume).

Non-limiting examples of binding agents include an antibody, an antibody fragment, a quenchbody, an analyte-specific antibody pair, or an antibody labeled with an enzyme.

Figure 3:
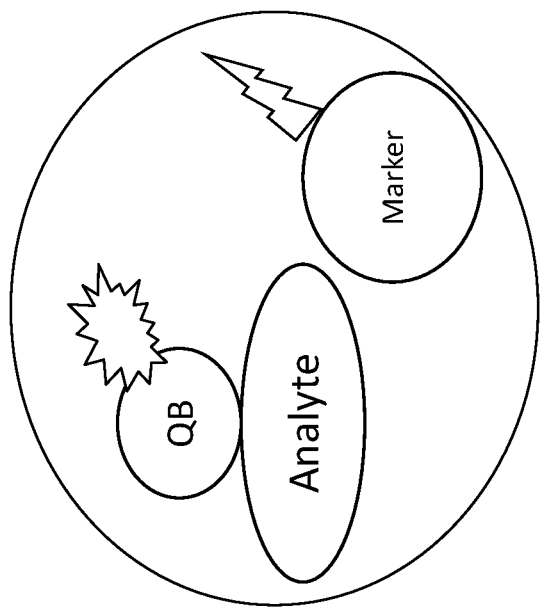
FIG. 3 depicts "Scheme 1" for detecting an analyte. According to this scheme, a partition is formed having an analyte (or antigen), a quenchbody (QB) capable of emitting a fluorescent signal when bound to the analyte and a marker capable of identifying the partition. The QB is allowed to bind to the analyte. When the partition is exposed to light, the QB emits a fluorescent signal and the marker emits a luminescent signal. The presence of the analyte is detected by detecting the fluorescent signal. The partition is also identified by detecting the luminescent signal.
Figure 3:
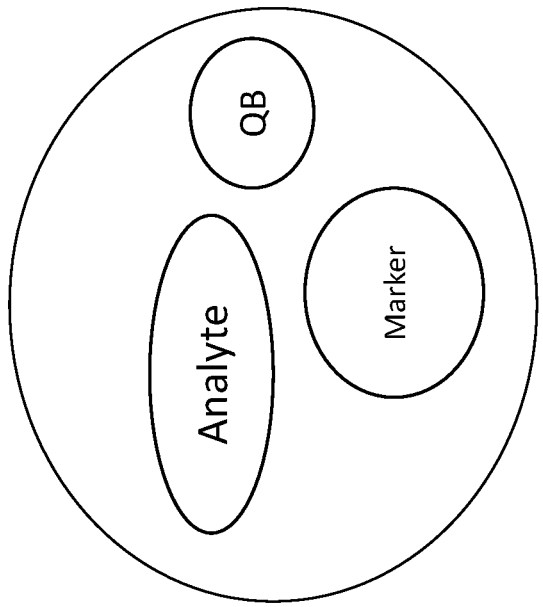

As used herein, a "quenchbody" refers to a molecule having (a) an antibody light-chain variable region polypeptide (e.g., $V_L$ polypeptide) and (b) an antibody heavy chain variable region polypeptide (e.g., $V_H$ polypeptide) in which either (a) or (b) is labeled with a fluorescent dye and the (a) or (b) not labeled with the fluorescent dye comprises a tryptophan amino acid at a sequence position such that, when the molecule is not bound to an analyte (or antigen), a fluorescence signal from the molecule is quenched. Referring to FIG. 3, when the molecule binds to the analyte, photoinduced electron transfer (PET) occurs between the fluorescent dye and the tryptophan amino acid and the fluorescence signal is unquenched (i.e., the fluorescence signal is detected). In an embodiment, the quenchbody is 5-carboxytetramethylrhodamine (TAMRA)-labeled anti-human osteocalcin (bone gla protein, BGP) scFv in which either the $V_L$ polypeptide or $V_H$ polypeptide of the anti-BGP scFv is labeled with TAMRA. See, for example, Abe et al. (2011) J. Am. Chem. Soc. 133:17386-17394.

Figure 4:
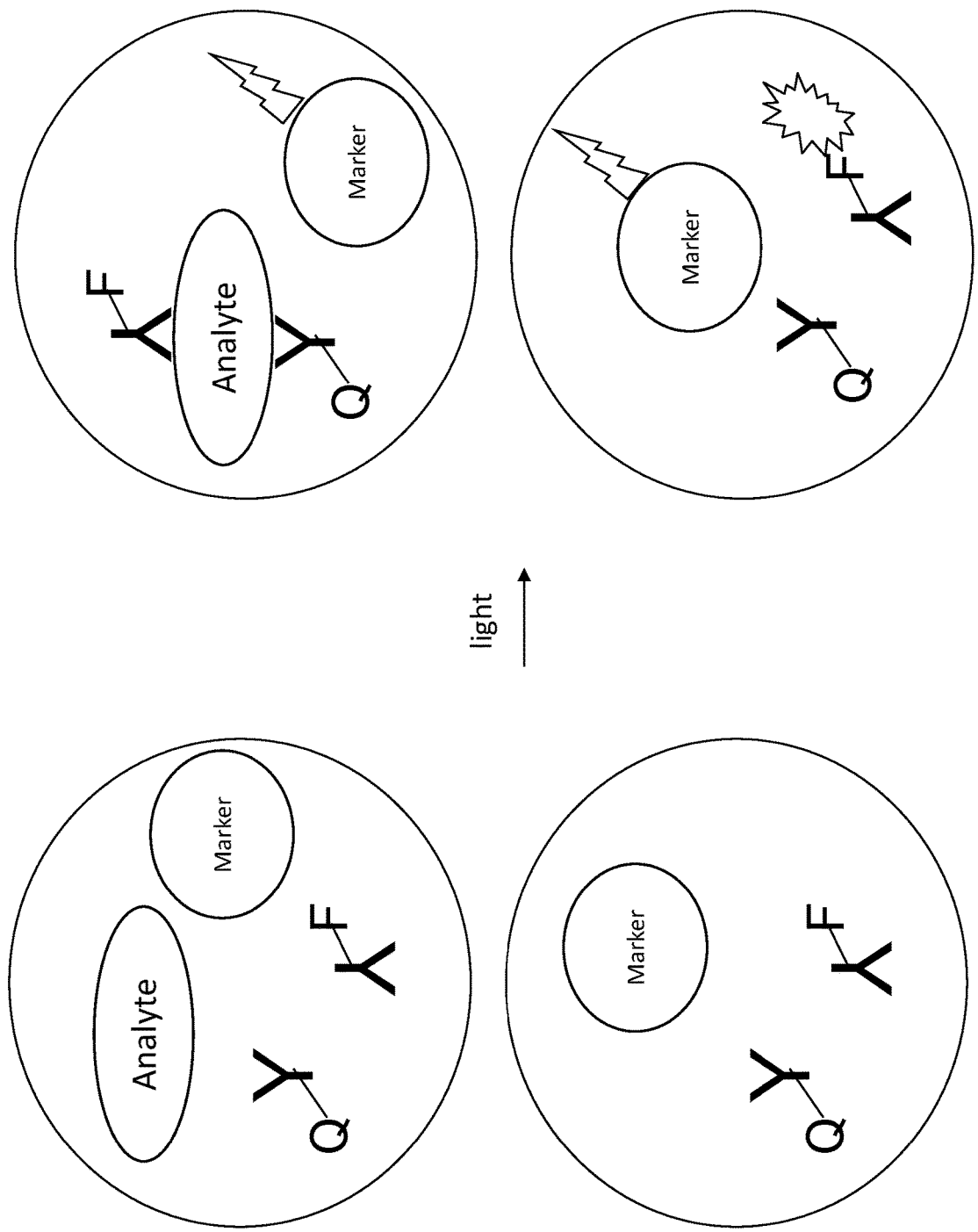
FIG. 4 depicts "Scheme 2" for detecting an analyte. According to this scheme, a partition is formed having an analyte, an antibody pair specific for the analyte (e.g., a first antibody labeled with a fluorophore F and a second antibody labeled with a quencher Q and a marker. The antibody pair is allowed to bind to the analyte. When the partition is exposed to light, the quencher Q quenches the fluorescence signal emitted by the fluorophore F. The presence of analyte is detected by quenching of the fluorescence signal. The absence of the analyte is detected by detecting a fluorescence signal. The partition is also identified by detecting the luminescent signal.

In certain embodiments, the analyte-specific antibody pair comprises a first antibody having a fluorescent label F and a second antibody having a quencher Q (see FIG. 4). Each of the antibodies binds to a different epitope on the analyte. When the analyte-specific antibody pair is bound to the analyte, the fluorescent signal from the first antibody is quenched by the second antibody. In some embodiments, the fluorescent signal from the first antibody is quenched by at least 10 percent to 25 percent by the second antibody. In the absence of the analyte, the fluorophore emits a fluorescent signal.

The first or second antibody can be labeled with any detectable label as described herein. In some embodiments, the first antibody is labeled with a fluorescent molecule. Examples of suitable fluorescent molecules that generate a fluorescent signal are described previously. In some embodiments, the second antibody is labeled with a nonfluorescent substance (i.e., a "quencher") that quenches the fluorescent signal generated by the fluorescent molecule. In some embodiments, the first antibody is labeled with a quencher and the second antibody is labeled with a fluorescent molecule. In some embodiments, the fluorescent signal generated by the fluorescent molecule is present or relatively increased when the quencher is not in close proximity to the fluorescent molecule, and the fluorescent signal generated by the fluorescent molecule is absent or relatively decreased when the quencher is brought into close proximity with the fluorescent molecule (e.g., by the first and second antibodies binding to adjacent epitopes on the target antigen). Non-limiting examples of useful quenchers include TAMRA (and other rhodamines), DABCYL, QSY™ quenchers (e.g., QSY 7 and QSY 21) (Molecular Probes, Eugene, Oreg.), Black-Hole Quenchers™ (BHQ) (Biosearch Technologies, Inc., Novato, Calif.), IowaBlack™ (Integrated DNA Tech., Inc., Coralville, Iowa), BlackBerry™ Quencher 650 (BBQ-650) (Berry & Assoc., Dexter, Mich.), paramagnetic ions, gold nanoparticles, Texas red, β-phycoerythrin, and β-phycoerythrin. Suitable fluorescent donor/quencher pairs include, but are not limited to, FAM/DABCLY, FAM/TAMRA, EDANS/DABCYL, Texas Red/DABCYL, BODIPY/DABCYL, Lucifer yellow/DABCYL, coumarin/DABCYL, fluorescein/QSY 7 dye, fluorescein/Texas red, pyrene butyrate/β-phycoerythrin, fluorescein/4',5'-dimethoxy-6-carboxyfluorescein, and fluorescein/rhodamine.

Figure 5:
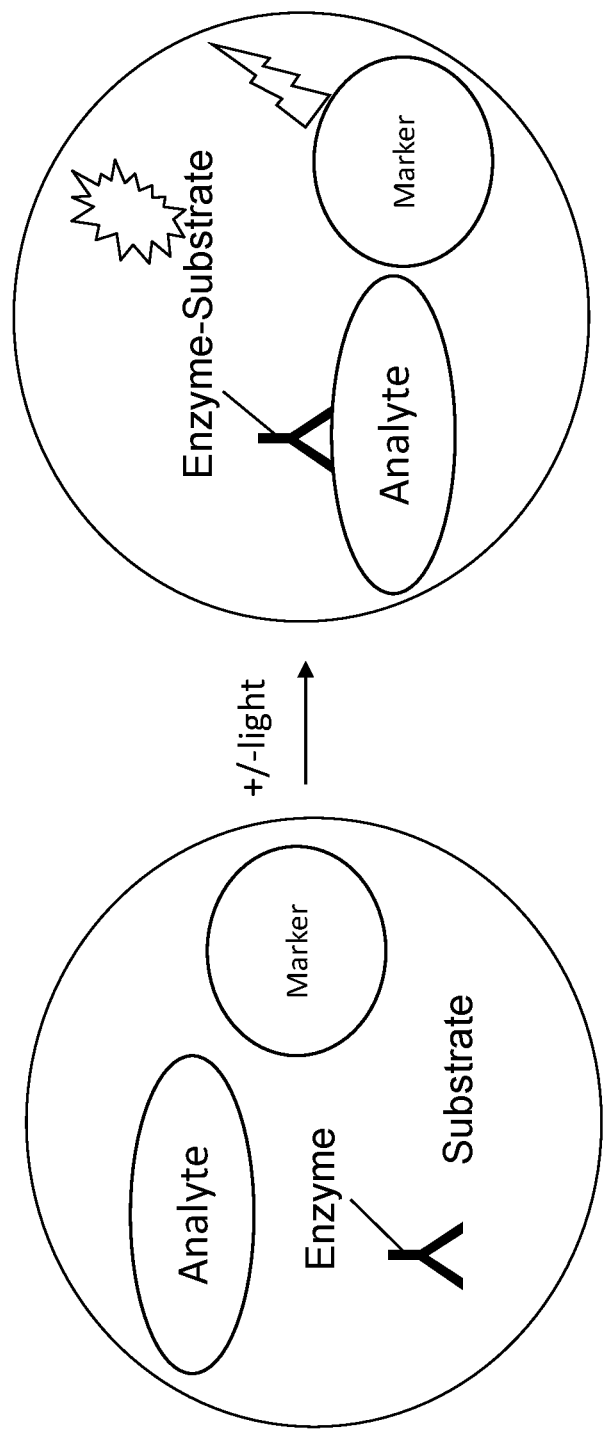
FIG. 5 depicts "Scheme 3" for detecting an analyte. According to this scheme, a partition is formed having an analyte, an enzyme-labeled antibody, a substrate, and a marker is formed. The enzyme-labeled antibody is allowed to bind to the analyte, the substrate is cleaved by the enzyme label to yield a product that emits a measurable signal. The presence of the analyte is detected by detecting the emitted signal. The partition is also identified by detecting the luminescent signal.

In an embodiment in which the binding agent is an antibody having an enzyme label, the presence of the label (e.g., in an analyte-antibody-enzyme label complex) is detected by detecting a product generated by the enzyme and a substrate (see FIG. 5). In some embodiments, the enzyme is capable of converting the substrate into an intermediate that is further converted into the molecule that produces the signal. Examples of suitable enzymes include, but are not limited to, a polymerase (e.g., DNA polymerase), urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-f3-D-galactopyranoside (ONPG), which yields a soluble product detectable at 410 nm. A urease detection system can be used with a substrate such as urea-bromocresol purple (Sigma Immunochemicals; St. Louis, Mo.). Other enzymes (e.g., alkaline phosphatase, β-galactosidase, β-glucuronidase, β-glucosidase, arylesterase, arylsulfatase, or neuramidase) can each be detected with a detection system that uses a chemiluminescent 1,2 dioxetane-based substrate (Michigan Diagnostics; Royal Oak, Mich.), each of which yield a soluble product detectable at 450 nm.

Techniques for attaching detectable labels to binding agents are well known. For example, a review of common protein labeling techniques can be found in Biochemical Techniques: Theory and Practice, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996). The techniques are also available as parts of commercially available kits (e.g., Thunder-Link® and Lightning-Link® from Innova Biosciences Ltd., Cambridge, United Kingdom). In some embodiments, a detectable label is attached to the binding agent via a covalent bond, ionic bond, hydrogen bonding, or by Van der Waals interactions.

Partition Marker

Partitions as described herein can contain markers to identify reagents (e.g., multiple binding agents) within a particular partition. For example, in some embodiments, one or more identifiers (e.g., dyes) can be inserted into each different partition such that each partition is represented by a pre-determined and known unique signal based on the one or more markers in the partition. As an example, by providing four different dyes at eight different dye concentrations, one can generate $8^4$ (=4096) different unique identifiers, each of which can be used to identify a unique partition (or partition set).

In some embodiments, the marker comprises one or more selectively absorbent molecule. A "selectively absorbent molecule", as used herein, is a molecule that absorbs certain characteristic colors or wavelengths of light while allowing other colors or wavelengths of light to pass or transmit through the molecule when a broadband light source is directed at the molecule. One of skill in the art will know and appreciate the numerous selectively absorbent molecules that may be used to comprise the selectively absorbent substance/constituent according to embodiments of the invention, including but not limited to, those commercially available from Exciton (Dayton, Ohio) and QCR Solutions, Corp. (Port St. Lucie, Fla.).

In some embodiments, the marker comprises one or more fluorescent molecules (e.g., fluorophore). In an embodiment, two different squaric acid dyes are used as markers. In an embodiment, a first marker is a red fluorescent dye (e.g., 1,3-bis [(1,3-dihydro-1,3,3-trimethyl-2H-indol-2-ylidene) methyl]-2,4-dicyclobutenediylium, bis(inner salt)) and a second marker is an orange fluorescent dye (e.g., 2-(3,5-dimethylpyrrol-2-yl)-4-(3,5-dimethyl-2H-pyrrol-2-ylidene)-3-hydroxy-2-cyclobuten-1-one). The peak emission of dye #1 is 585 nm, and the peak emission of dye #2 is 630 nm. Examples of suitable fluorophores are described above.

The concentration of fluorescent dyes required to label partitions is dependent on the detection system used. For example, the dye concentration in partitions in some embodiments ranges from 10 nM to 1000 nM for non-protein dyes and from 0.1 ug/ml to 50 ug/ml for protein dyes or dyes that are conjugated to fluorescent proteins. Different detection systems may require higher or lower dye concentrations.

Surfactant

Partitions as described herein can contain one or more surfactants to reduce coalescence of droplets during transport. As used herein, a "surfactant" is a surface-active substance capable of reducing the surface tension of a liquid in which it is present. A surfactant, which also or alternatively may be described as a detergent and/or a wetting agent, may incorporate both a hydrophilic portion and a hydrophobic portion, which may collectively confer a dual hydrophilic-hydrophobic character on the surfactant. A surfactant may, in some cases, be characterized according to its hydrophilicity relative to its hydrophobicity. In some embodiments, the aqueous phase incorporates at least one hydrophilic surfactant. The aqueous phase may include at least one nonionic surfactant and/or ionic surfactant. In certain embodiments, the aqueous phase includes a surfactant that is a block copolymer of polypropylene oxide and polyethylene oxide. In some embodiments, the surfactant is a block copolymer of polypropylene oxide and polyethylene oxide sold under the trade names PLURONIC and TETRONIC (BASF). In some embodiments, the surfactant is a nonionic block copolymer of polypropylene oxide and polyethylene oxide sold under the trade name PLURONIC F-68. In some embodiments, the surfactant of the aqueous phase is a water-soluble and/or hydrophilic fluorosurfactant. Exemplary fluorosurfactants for the aqueous phase are sold under the trade name ZONYL (DuPont), such as ZONYL FSN fluorosurfactants. In some cases, the surfactant may include polysorbate 20 (sold under the trade name TWEEN-20 by ICI Americas, Inc.). The concentration of a particular surfactant or total surfactant present in the aqueous phase may be selected to stabilize emulsion droplets prior to heating. In some embodiments, the concentration of surfactant for the aqueous phase is 0.01 to 10%, 0.05 to 5%, 0.1 to 1%, or 0.5% by weight.

B. Binding

In exemplary step 120, the binding agent is allowed to bind to the analyte. In some embodiments, the binding agent is incubated with the sample in the partition for about 5 minutes to about 60 minutes to allow the binding agent to bind to the analyte.

C. Detection

In exemplary step 130, the presence of the analyte is detected by detecting a signal emitted from the partition or by detecting quenching of the fluorescent signal from the partition (see FIG. 2, C). The level and identity of the marker in the partition is also detected, thereby providing the identity of the binding agent (and the analyte) in the partition.

In certain embodiments, the analyte in the sample is quantified by using a standard curve generated with known amounts of analyte. The process of quantifying the analyte using a standard curve may include measuring the fluorescent signal intensity generated from at least two known amounts of analyte and then plotting the fluorescent signal intensities as a function of analyte concentration. The analyte concentration in the sample is then determined by using the measured fluorescent signal intensity generated by the binding agent bound to the analyte and obtaining the concentration of the analyte from the standard curve.

In some embodiments, a digital readout assay (e.g., digital analysis) can be used to detect and quantify one or more antigens in a sample by partitioning at least the labels from the separated sample (e.g., labels in antigen-affinity agent-label complexes) and identifying the partitions containing the label. Generally, the process of digital analysis involves determining for each partition of a sample whether the partition is positive or negative for the presence of the label or labels to be detected. For quantifying the amount of antigen in a sample (e.g., quantifying the concentration of an antigen in a sample), the partitions are examined for the presence or absence of a detectable signal in each partition. A partition is "positive" for the presence of the antigen if a signal is detected in the partition. In some embodiments, the signal that is detected in the partition is generated by a label linked to an affinity agent in an antigen-affinity agent-label complex (e.g., a fluorescent, chemiluminescent, radioactive, or enzymatic label linked to the affinity agent). A partition is "negative" for the presence of the antigen if no signal is detected in the partition. In some embodiments in which a non-endpoint reaction condition is used, differences in the signal may be detected between partitions and may be used to differentiate the partitions.

In some embodiments, a detector that is capable of detecting a signal or multiple signals is used to analyze each partition for the presence or absence of the antigen. For example, in some embodiments a two-color reader (fluorescence detector) is used. The fraction of positive-counted partitions can enable the determination of absolute concentrations for the antigen or antigens to be measured.

In some embodiments, once a binary "yes-no" result has been determined for each of the partitions of the sample, the data for the partitions is analyzed using an algorithm based on Poisson statistics to quantify the amount of antigen in the sample. Statistical methods for quantifying the concentration or amount of an antigen or antigens is described, for example, in WO 2010/036352, which is incorporated by reference herein in its entirety.

III. Partition Libraries

Also provided are partition libraries comprising a plurality of partitions for carrying out the methods as described herein. In some embodiments, the partition library comprises two or more partitions, wherein at least some partitions of the library (e.g., at least 5%, 10%, 15%, 20%, 25%, 30%, 35%, 40%, 45%, 50%, 55%, 60%, 65%, 70%, 75%, 80%, 85%, 90%, or 95% of the partitions in the library) comprise at least one, two, three, four, five or more binding agents.

In some embodiments, the partition library comprises at least 500, 1000, 2000, 3000, 4000, 5000, 6000, 7000, 8000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 10,000,000, 20,000,000, 30,000,000, 40,000,000, 50,000,000, 60,000,000, 70,000,000, 80,000,000, 90,000,000, 100,000,000, 150,000,000, or 200,000,000 partitions.

In some embodiments, the library of partitions further comprise one or more markers (or dyes) for determining the identity of the binding agent in the partition. Thus for example, if there are n different sets of binding agent represented in the partitions, there will be n different spectroscopically distinguishable characteristics, with each different set assigned to a particular characteristic. As noted above, this can be achieved, for example, by providing 1, 2, 3, 4, 5 or more different detectable dyes, each at one or 2, 3, 4, 5, 6, 7, 8, 9, 10, or more concentrations, such that combination of the concentrations of the dyes provides a unique spectroscopically distinguishable characteristics for each binding agent partition set. Methods and systems for monitoring combinations of spectroscopic intensity are described in, e.g., WO 2012/135327.

In some embodiments, the partition library comprises a plurality of partitions that are solid partitions (e.g., wells or tubes). In some embodiments, the partitions are microchannels. In some embodiments, the partition library comprises a plurality of partitions that are fluid partitions (e.g., aqueous droplets within an oil phase). In some embodiments, the partitions are droplets. In some embodiments, the partitions are microcapsules. Examples of suitable partitions and methods of generating partitions are described above.

In some embodiments, the partition library comprises partitions that are substantially uniform in shape and/or size. For example, in some embodiments, the partitions (e.g., droplets) are substantially uniform in average diameter. In some embodiments, the partitions (e.g., droplets) have an average diameter of about 0.001, 0.005, 0.01, 0.05, 0.1, 0.5, 1, 5, 10, 20, 30, 40, 50, 60, 70, 80, 90, 100, 150, 200, 300, 400, 500, 600, 700, 800, 900, or 1000 microns. In some embodiments, the partitions (e.g., droplets) have an average diameter of less than about 1000, 900, 800, 700, 600, 500, 400, 300, 200, 100, 50, or 25 microns. In some embodiments, the partition library comprises partitions (e.g., droplets) that are non-uniform in shape and/or size.

In some embodiments, the partitions (e.g., droplets) are substantially uniform in volume. For example, in some embodiments, the partitions (e.g., droplets) have an average volume of about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, or 50 nL.

In some embodiments, the partitions (e.g., droplets) are stable and are capable of long-term storage. In some embodiments, the partitions can be stored at about −70°, −20°, 0°, 3°, 4°, 5°, 6°, 7°, 8°, 9°, 10°, 15°, 20°, 25°, 30°, 35°, or 40° C. for an extended period of time (e.g., for at least 30 days, at least 60 days, at least 90 days, or longer).

IV. Kits

In another aspect, kits for detecting an analyte according to the methods described herein are provided. In some embodiments, a kit comprises one or more binding agents as described herein, e.g., one or more quenchbodies, antibodies labeled with an enzyme, and/or analyte-specific antibody pair as described herein. In embodiments having an antibody labeled with an enzyme, a kit further comprises a substrate. In some embodiments, a kit further comprises assay components (e.g., buffers, buffer salts, and/or surfactants). In some embodiments, a kit for detecting an analyte further comprises the analyte to which the binding specifically binds. In some embodiments, a kit further comprises instructions for carrying out the methods described herein.

V. Systems

Also provided are systems for performing the methods described herein. In some embodiments, the systems include one or more reservoirs comprising reaction components or a plurality of partitions (e.g., droplets) as described herein (see, e.g., FIG. 2, Reservoir A). In some embodiments, the system further comprises one or more microfluidic channels providing fluid communication between the one or more reservoirs and a detector (s). In some embodiments, all of the above described components are provided as part of a single cartridge. In some embodiments, the cartridge can in turn be inserted into a manifold allowing for attachment to one or more pumps configured to pump the droplets through the microfluidic channels.

In some embodiments, the system further comprises one or more droplet injectors (e.g., injectors B). In some embodiments, the system comprises one or more droplet injectors configured to inject one or more of a sample, binding agent and/or marker into partitions. Droplet injectors are described in, e.g., WO 2012/135259, US 2012/0132288, each of which is incorporated by reference in its entirety.

Exemplary system components are described in, e.g., US2011/0151578, US2011/0218123, US2012/0222748, US2011/0218123, US 2012/0222748, WO2012/135201, WO2012/135259, WO2014/043388, WO 2012/135327.

Detectors as described herein can detect one or both of signals from (i) the binding agent label and/or (ii) the marker that identifies the partition. In some embodiments, the droplets in an emulsion flow through microfluidic channels passing an optical detector that measures a fluorescent signal coming from the assay. In some embodiments, multiple sets of measurements of the same target molecule signal over time are generated and aggregated.

The spectroscopic intensity and wavelength of the labels and/or markers may be measured by any methods for spectroscopic analysis known and appreciated by one of ordinary skill in the art. Spectroscopic methods that may be utilized in the present invention include, but are not limited to, a laser and photodetector pair system or more complex optics known to those of skill in the art where the path of an optical beam intersects with the path of a spectroscopic substance and the excitation or illumination of the labels and/or markers is captured by an optical path comprising one or more objectives, mirrors, and/or lenses to direct the light to a photomultiplier tube (PMT) or photosensitive camera. In an embodiment, the fluoroscopy method uses flow cytometry instrumentation. The spectroscopic intensity measurements may comprise one or more methods, including but not limited to, light scatter, absorption, chemiluminescence, fluorescent intensity, radiation decay counts, colorimetric. Samples to be tested are placed in the path of an excitation energy source such as a light source selected from but is not limited to, lasers, light-emitting diodes (LEDs), arc lamps, broadband light source, and high intensity light bulbs. The labels and/or markers in the partition to be tested scatter, absorb, chemiluminesce, or fluoresce (also referred to herein as "signal") in the form of light at a wavelength substantially different from the wavelength of the light source. This light from the partition to be tested is then captured by a detector or sensor, which may be selected from but is not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, photomultiplier tubes (PMTs), or photomultiplier tube arrays.

Known optical or electronic means may be optionally used to amplify the light from the light source and/or the light from the sample to be tested and/or to separate one or both into its component wavelengths.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria.

Microfluidic systems may be provided that are able to cause two or more droplets to fuse or coalesce into one droplet, for example, in cases where the two or more droplets ordinarily are unable to fuse or coalesce, for example due to composition, surface tension, droplet size, etc. as known to those of ordinary skill in the art. The fluidic droplets may be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference. As an example, in microfluidic systems, the surface tension of the droplets, relative to the size of the droplets may prevent fusion or coalescence of the droplets from occurring. In one embodiment, two droplets may be given opposite electrical charges (i.e., positive and negative charges, not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may be passed through a capacitor, a chemical reaction may occur to cause the droplets to become charged, flowing the droplets over a region with opposite wetting properties, etc.

The "cross-sectional dimension" of the channel is measured perpendicular to the direction of fluid flow. In some embodiments, the fluid channels have maximum cross-sectional dimensions less than about 2 mm, and in some cases, less than about 1 mm. In one set of embodiments, all fluid channels are microfluidic or have a largest cross sectional dimension of no more than about 2 mm or about 1 mm. In certain embodiments, the fluid channels may be formed in part by a single component (e.g. an etched substrate or molded unit). Larger channels, tubes, chambers, reservoirs, etc. can be used to store fluids in bulk and to deliver fluids to components of the invention. In some embodiments, the maximum cross-sectional dimension of the channels) containing embodiments of the invention are less than about 500 microns, less than about 200 microns, less than about 100 microns, less than about 50 microns, or less than about 25 microns.

A "channel." as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least about 2:1, more typically at least about 3:1, at least about 5.1, or at least about 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or about 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion." published as U S Patent Application Publication No. 2005/0172476 on Aug. 11, 2005; U.S. patent application Ser. No. 11/360,845, filed Feb. 23, 2006, entitled "Electronic Control of Fluidic Species." published as U.S. Patent Application Publication No. 2007/000342 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007; U.S. Provisional Patent Application Ser. No. 60/920,574, filed Mar. 28, 2007, entitled "Multiple Emulsions and Techniques for Formation"; and International Patent Application No. PCT/US2006/001938, filed Jan. 20, 2006, entitled "Systems and Methods for Forming Fluidic proplets Encapsulated in Particles Such as Colloidal Particles," published as WO 2006/078841 on Jul. 27, 2006, each incorporated herein by reference in their entireties.

Computer Implemented Methods and Systems

Any of the methods described herein may be totally or partially performed with a computer system including one or more processors, which can be configured to perform the steps of the methods. Thus, embodiments can be directed to computer systems configured to perform the steps of any of the methods described herein, potentially with different components performing a respective step or a respective group of steps. Although presented as numbered or ordered steps, steps of the methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In some embodiments, the computer implemented method is implemented by a computer system that is in electronic communication with a detector that is capable of detecting optically labeled binding agents bound to, for example, an analyte in a channel of a microfluidic device or in an image of a microfluidic device.

The disclosure further provides a computer product that is capable of performing any one of or all of the steps of the methods described herein. Thus, in some embodiments, the computer product comprises a non-transitory computer readable medium storing a plurality of instructions for controlling a processor to perform an operation of one or more of the method steps described herein.

Figure 6:
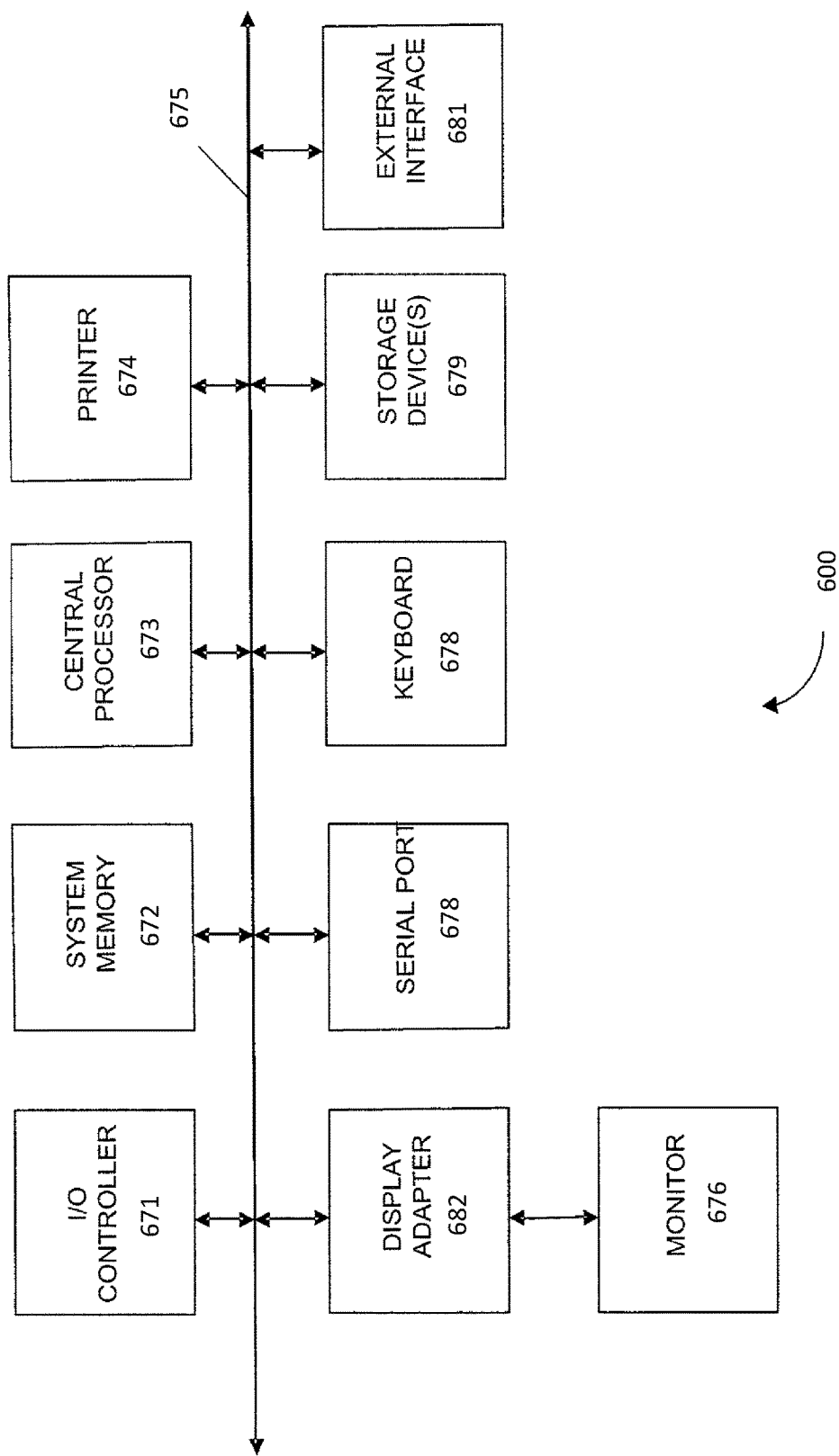
FIG. 6 shows a block diagram of an example computer system usable with the methods and systems according to embodiments of the invention.

FIG. 6 shows a block diagram of an example computer system 600 usable with methods and system according to embodiments of the invention.

Any of the computer systems mentioned herein may utilize any suitable number of subsystems. Examples of such subsystems are shown in FIG. 6 in computer apparatus 600. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 6 are interconnected via a system bus 675. Additional subsystems such as a printer 674, a keyboard 678, a storage device(s) 679, a monitor 676, which is coupled to a display adapter 682, and others are shown. Peripherals and input/output (I/O) devices, which couple to I/O controller 671, can be connected to the computer system by any number of means known in the art, such as a serial port 677. For example, the serial port 677 or an external interface 681 (e.g. Ethernet, Wi-Fi, etc.) can be used to connect the computer system 600 to a wide area network such as the Internet, a mouse input device, or a scanner. The interconnection via the system bus 675 allows the central processor 673 to communicate with each subsystem and to control the execution of instructions from the system memory 672 or the storage device(s) 679 (e.g., a fixed disk, such as a hard drive or optical disk), as well as the exchange of information between subsystems. The system memory 672 and/or the storage device(s) 679 may embody a computer readable medium. Any of the data mentioned herein can be output from one component to another component and can be output to the user.

A computer system can include a plurality of the same components or subsystems, e.g., connected together by the external interface 681 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that the embodiments described above can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

EXAMPLES

The following examples are provided by way of illustration only and not by way of limitation. Those of skill in the art will readily recognize a variety of non-critical parameters that could be changed or modified to yield essentially the same or similar results.

Example 1

Scheme 1 for Detecting an Analyte

This example illustrates detecting an analyte of interest in a sample using a quenchbody that specifically binds to the analyte. In this scheme, a partition having a sample containing osteocalcin, a quenchbody (i.e., TAMRA-labeled anti-human osteocalcin scFv), and two fluorescent markers is formed. The fluorescent markers are: 1,3-bis [(1,3-dihydro-1,3,3-trimethyl-2H-indol-2-ylidene)methyl]-2,4-dicyclobutenediylium, bis(inner salt) with a peak emission of 585 nm and 2-(3,5-dimethylpyrrol-2-yl)-4-(3,5-dimethyl-2H-pyrrol-2-ylidene)-3-hydroxy-2-cyclobuten-1-one having a peak emission of 630 nm. The quenchbody is allowed to bind to the osteocalcin, photoinduced electron transfer occurs between the TAMRA fluorescent dye and a tryptophan amino acid. A fluorescence signal is unquenched and is detected by methods described herein. The presence of osteocalcin in the partition is determined by digital analysis or the osteocalcin concentration is determined by standard curve analysis, both methods of which are described herein. See FIG. 3.

Example 2

Scheme 2 for Detecting an Analyte

This example illustrates detecting an analyte of interest (interferon gamma) using an antibody pair that specifically binds to the analyte (e.g., each anti-interferon gamma antibody in the pair binds to different epitopes on interferon gamma). In this scheme, a partition having a sample containing interferon gamma, an antibody pair specific for the interferon gamma (e.g., an antibody labeled with FAM, a fluorophore F, and an antibody labeled with TAMRA, a quencher Q) and the two fluorescent markers described in Example 1 is formed. The antibody pair is allowed to bind to the interferon gamma, and the presence of interferon gamma is detected by quenching of the fluorescence signal. The quenching of the fluorescence signal is by at least 10 percent to 25 percent. Thus, the fluorescence signal intensity is inversely related to the amount of interferon gamma present in the sample. The presence of the interferon gamma in the partition is determined by digital analysis or the interferon gamma concentration is determined by standard curve analysis, both methods of which are described herein. See FIG. 4.

Example 3

Scheme 3 for Detecting an Analyte

This example illustrates detecting an analyte of interest using an enzyme-labeled antibody that specifically binds to the analyte. In this scheme, a partition having a sample containing the analyte, an enzyme-labeled antibody (e.g., an antibody labeled with β-galactosidase), a chromogenic substrate (e.g., o-nitrophenyl-f-D-galactopyranoside or ONPG)

and the two fluorescent markers described in Example 1 is formed. The enzyme-labeled antibody is allowed to bind to the analyte, the ONPG is cleaved by the enzyme to yield galactose and o-nitrophenol which has a yellow color. The yellow color is detected at 410 nm and is proportional to the concentration of antigen present in the sample. Alternatively, the presence of the antigen in the partition is determined by digital analysis by methods described herein. See FIG. 5.

All patents, patent applications, and other published reference materials cited in this specification are hereby incorporated herein by reference in their entirety.

What is claimed is:

1. A method of detecting an analyte in a sample, the method comprising:
   forming a fluid partition comprising the sample, a binding agent that emits a signal when bound to the analyte, and a marker that identifies the partition;
   allowing the binding agent to bind to the analyte, if present; and
   detecting the presence of the analyte in the sample by detecting the signal emitted from the binding agent in the partition and the marker.

2. The method of claim 1, wherein the binding agent is a quenchbody.

3. The method of claim 1 wherein the partition further comprises a substrate and the binding agent is an antibody labeled with an enzyme capable of converting the substrate into a molecule that produces a signal when the antibody binds to the analyte.

4. The method of claim 3, wherein the enzyme is capable of converting the substrate into an intermediate that is further converted into the molecule that produces the signal.

5. The method of claim 1, wherein the forming a partition step comprises injecting the sample, binding agent and marker into the partition in any order or simultaneously.

6. The method of claim 1, wherein the forming a partition step comprises forming a sample partition and injecting the binding agent and the marker into the sample partition.

7. The method of claim 1 wherein the forming a partition step comprises forming a binding agent partition and injecting the sample and the marker into the binding agent partition.

8. The method of claim 1, wherein the marker is a fluorophore.

9. A method of detecting an analyte in a sample, the method comprising:
   forming a partition comprising the sample, a binding agent that quenches a fluorescent signal when bound to the analyte, and a marker that identifies the partition;
   allowing the binding agent to bind to the analyte, if present; and
   detecting the presence of the analyte in the sample by detecting the marker from the partition and the quenching of the fluorescent signal from the binding agent in the partition.

10. A method of detecting an analyte in a sample, the method comprising:
    forming a partition comprising the sample, a marker that identifies the partition and a quenchbody that emits a fluorescent signal when bound to the analyte;
    allowing the quenchbody to bind to the analyte, if present; and
    detecting the presence of the analyte in the sample by detecting the marker from the partition and the fluorescent signal emitted from the quenchbody in the partition.

11. The method of claim 10, wherein the forming a partition step comprises injecting the sample and the quenchbody into the partition in any order or concurrently.

12. The method of claim 10, wherein the forming a partition step comprises forming a sample partition followed by injecting the quenchbody into the sample partition.

13. The method of claim 10, wherein the forming a partition step comprises forming a quenchbody partition followed by injecting the sample into the quenchbody partition.

14. The method of claim 10, further comprising injecting the partition with a marker that identifies the partition; and responsive to detecting the marker, identifying the partition.

15. The method of claim 14, wherein the marker is a fluorophore.

16. The method of claim 1, wherein the partition is a droplet surrounded by a carrier fluid.

17. The method of claim 16, wherein the carrier fluid is oil.

18. The method of claim 1, wherein the analyte is selected from the group consisting of proteins, peptides, hormones, antibodies and antibody fragments.

19. The method of claim 1, wherein the sample is selected from the group consisting of a protein solution, a peptide solution, cell extract, whole blood, plasma, serum, saliva, urine, milk, eggs and water.

* * * * *